United States Patent [19]

Eckhardt et al.

[11] Patent Number: 4,721,797
[45] Date of Patent: Jan. 26, 1988

[54] PROCESS FOR THE PREPARATION OF N-ACYL-N-ALKYL-2,6-DIALKYL-3-CHLOROANILINES

[75] Inventors: Wolfgang Eckhardt, Lörrach, Fed. Rep. of Germany; Hans Süess, Möhlin, Switzerland

[73] Assignee: Ciba-Geigy Corporation, Ardsley, N.Y.

[21] Appl. No.: 903,626

[22] Filed: Sep. 2, 1986

[51] Int. Cl.$^4$ ............... C07C 102/00; C07D 307/16
[52] U.S. Cl. .................... 549/493; 549/321; 560/43; 562/433; 562/455; 562/456; 564/135; 564/143; 564/207; 564/214
[58] Field of Search .............. 549/321, 493; 560/43; 562/433, 455, 456; 564/135, 143, 207, 214

[56] References Cited

U.S. PATENT DOCUMENTS 3,933,860  1/1976  Chan ................................. 549/321
4,564,629  1/1986  Kunz et al. ........................ 514/472

FOREIGN PATENT DOCUMENTS 0028011  5/1981  European Pat. Off. .
1455471  11/1976  United Kingdom .
2006783  5/1979  United Kingdom .
2098210  11/1982  United Kingdom .

OTHER PUBLICATIONS

Synthesis, 1971, p. 467.

Primary Examiner—Richard L. Raymond
Attorney, Agent, or Firm—Karl F. Jorda

[57] ABSTRACT

N-acyl-N-alkyl-2,6-dialkyl-3-chloroanilines of the formula

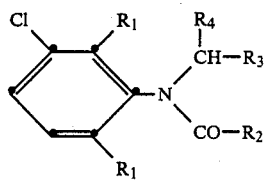

wherein $R_1$ is methyl or ethyl, $R_2$ is alkoxymethyl, chloromethyl or 2-tetrahydrofuryl, $R_3$ is alkoxymethyl, carboxy or alkoxycarbonyl and $R_4$ is hydrogen or methyl and, if $R_3$ is carboxy or alkoxycarbonyl, $R_4$ is also 2-alkoxyethyl and 2-alkoxypropyl, and $R_3$ and $R_4$, together with the carbon atom to which both radicals are attached, may also form a 2-oxotetrahydro-3-furyl radical or a 2-oxo-5-methyltetrahydro-3-furyl radical, are prepared by reacting a 2,6-dialkylaniline of the formula

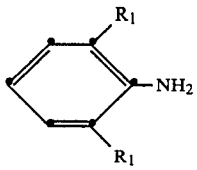

with a halide of the formula

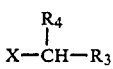

wherein X is chlorine or bromine, to give an N-alkyl-2,6-dialkylaniline of the formula

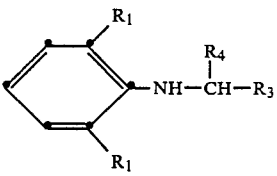

then converting said compound by further reaction with an acylating agent of the formula

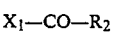

wherein $X_1$ is chlorine, bromine or -O-CO-$R_2$, into an N-acyl-N-alkyl-2,6-dialkylaniline of the formula

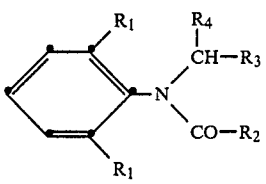

and subsequently converting said compound by reaction with chlorine into an N-acyl-N-alkyl-2,6-dialkyl-3-chloroaniline of the above formula.

27 Claims, No Drawings

PROCESS FOR THE PREPARATION OF N-ACYL-N-ALKYL-2,6-DIALKYL-3-CHLOROANILINES

The present invention relates to a process for the preparation of N-acyl-N-alkyl-2,6-dialkyl-3-chloroanilines of formula I

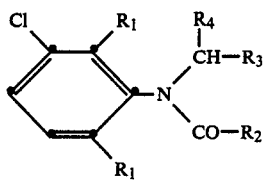

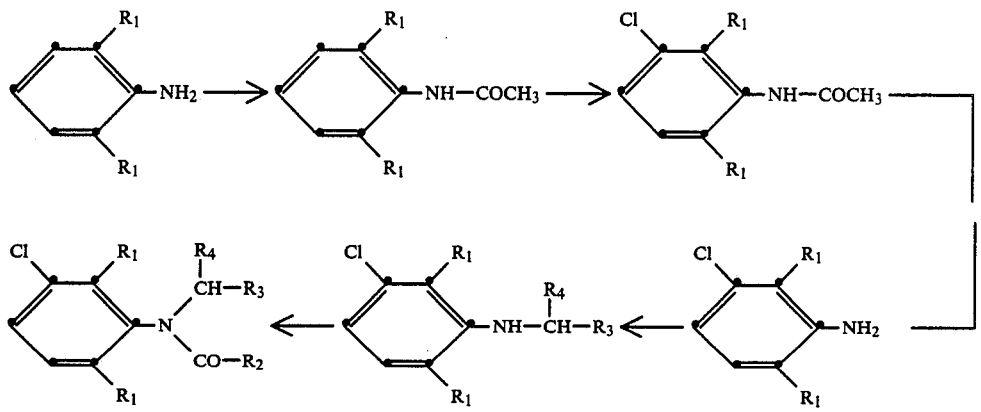

wherein $R_1$ is methyl or ethyl, $R_2$ is alkoxymethyl, chloromethyl or 2-tetrahydrofuryl, $R_3$ is alkoxymethyl, carboxy or alkoxycarbonyl and $R_4$ is hydrogen or methyl and, if $R_3$ is carboxy or alkoxycarbonyl, $R_4$ is also 2-alkoxyethyl and 2-alkoxypropyl, and $R_3$ and $R_4$, together with the carbon atom to which both radicals are attached, may also form a 2-oxotetrahydro-3-furyl radical or a 2-oxo-5-methyltetrahydro-3-furyl radical.

Some of the compounds of formula I have fungicidal activity and some of them have herbicidal activity. Compounds of this type are described for example in U.S. Pat. Nos. 4,564,629 and 3,933,860, British patent specification No. 1 455 471, published European patent application No. 0 028 011 and published British patent application No. 2 006 783.

It is known from published British patent application No. 2 098 210 to prepare N-acylated N-alkoxycarbonylmethyl-2,6-dialkyl-3-haloanilines and N-(1-alkoxycarbonylethyl)-2,6-dialkyl-3-haloanilines by reacting halogen with corresponding N-alkoxycarbonylmethyl-2,6-dialkylanilines and N-(1-alkoxycarbonylethyl)-2,6-dialkylanilines in the presence of at least 2 moles of Lewis acid per mole of N-alkoxycarbonylalkyl-2,6-dialkylaniline, and subsequently acylating the resultant N-alkoxycarbonylmethyl-2,6-dialkyl-3-haloanilines and N-(1-alkoxycarbonylethyl)-2,6-dialkyl-3-haloanilines. Suitable Lewis acids are aluminium chloride, aluminium bromide, boron trifluoride, tin tetrachloride and titanium tetrachloride. This process is disadvantageous in that very large amounts of Lewis acid have to be employed in order to obtain the desired effect. For example, 2 parts by weight of aluminium chloride are necessary per part of N-alkoxycarbonylalkyl-2,6-dialkylaniline. Since this large amount of aluminium chloride must first be decomposed with water before the reaction mixture is worked up, not only is the process costly with respect to the starting materials and auxiliaries required, but it is also complicated to perform.

It is also known to prepare 3-chloro-2,6-dimethylacetanilide in a yield of 80% of theory by chlorinating 2,6-dimethylacetanilide (q.v. Synthsesis, 1971, p. 467). In accordance with this method, the N-acyl-N-alkyl-2,6-dialkyl-3-chloroanilines of formula I are obtainable by acetylating a corresponding 2,6-dialkylaniline, chlorinating the 2,6-dialkylacetanilide, hydrolysing the resultant 3-chloro-2,6-dialkylacetanilide to give the 3-chloro-2,6-dialkylaniline, alkylating said compound and subsequently effecting acylation according to the following scheme:

In accordance with this method, the N-acyl-N-alkyl-2,6-dialkyl-3-chloroanilines of formula I can be prepared in a yield of about 40% of theory, based on the starting 2,6-dialkyldianiline. This method is complicated on account of the large number of reaction steps required and is unsatisfactory with respect to the yields which can be obtained.

It is therefore the object of the present invention to provide a process which makes it possible to prepare the N-acyl-N-alkyl-2,6-dialkyl-3-chloroanilines of formula I in simple manner and in good yield.

It has been found that this object can be advantageously accomplished by converting a corresponding 2,6-dialkylaniline by alkylation and subsequent acylation into a corresponding N-acyl-N-alkyl-2,6-dialkylaniline, and then converting said compound by reaction with chlorine into an N-acyl-N-alkyl-2,6-dialkyl-3-chloroaniline of formula I.

In accordance with the present invention, it is therefore proposed to prepare the N-acyl-N-alkyl-2,6-dialkyl-3-chloroanilines of formula I by reacting a 2,6-dialkylaniline of formula II

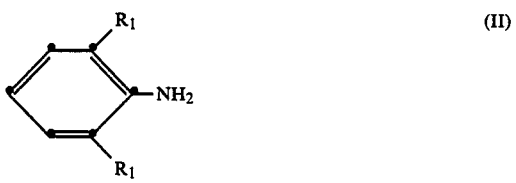

wherein $R_1$ is as defined for formula I, with a halide of formula III

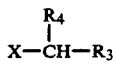

(III)

wherein $R_3$ and $R_4$ are as defined for formula I and X is chlorine or bromine, to give an N-alkyl-2,6-dialkylaniline of formula IV

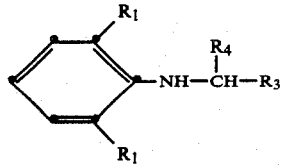

(IV)

wherein $R_1$, $R_3$ and $R_4$ are as defined for formula I, then reacting the N-alkyl-2,6-dialkylaniline of formula IV with an acylating agent of formula V

(V)

wherein $R_2$ is as defined for formula I and $X_1$ is chlorine, bromine or —O—CO—$R_2$, and subsequently converting the resultant N-acyl-N-alkyl-2,6-dialkylaniline of formula VI

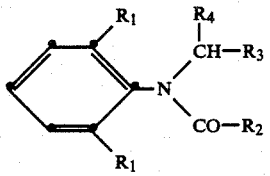

(VI)

wherein $R_1$, $R_2$, $R_3$ and $R_4$ are as defined for formula I, by reaction with chlorine into an N-acyl-N-alkyl-2,6-dialkyl-3-chloroaniline of formula 1.

Suitable 2,6-dialkylanilines of formula II are 2,6-dimethylaniline and 2,6-diethylaniline. 2,6-Dimethylaniline is particularly suitable.

Suitable halides of formula III are 2-alkoxyethyl chloride, 2-alkoxyethyl bromide, 2-alkoxypropyl chloride, 2-alkoxypropyl bromide, 2-chloroacetic acid, 2-bromoacetic acid, 2-chloropropionic acid, 2-bromopropionic acid, 2-chloroacetic acid alkyl esters, 2-bromoacetic acid alkyl esters, 2-chloropropionic acid alkyl esters, 2-bromopropionic acid alkyl esters, 2-chloro-4-alkoxybutyric acid, 2-bromo-4-alkoxybutyric acid, 2-chloro-4-alkoxyvaleric acid, 2-bromo-4-alkoxyvaleric acid, 2-bromo-4-alkoxybutyric acid alkyl esters, 2-bromo-4-alkoxybutyric acid alkyl esters, 2-chloro-4-alkoxyvaleric acid alkyl esters, 2-bromo-4-alkoxyvaleric acid alkyl esters, α-chloro-γ-butyrolactone, α-bromo-γ-butyrolactone, α-chloro-γ-valerolactone and α-bromo-γ-valerolactone. The alkoxy and alkyl ester groups present in said halides of formula III contain alkyl radicals each of 1 to 4 carbon atoms. Specifically, said alkyl radicals may be methyl, ethyl, propyl, isopropyl, butyl, sec-butyl, tert-butyl and isobutyl.

When using halides of formula III wherein X is chlorine, the reaction of a 2,6-dialkylaniline of formula II with the halide of formula III is advantageously carried out in the presence of an alkali metal iodide, in particular potassium iodide, as catalyst.

Preferred halides of formula III are 2-methoxyethyl chloride, 2-ethoxyethyl chloride, 2-methoxyl-methylethyl chloride, methyl 2-chloroacetate, ethyl 2chloroacetate methyl 2-bromopropionate, ethyl 2-bromopropionate and α-chloro-γ-butyrolactone. A particularly preferred halide of formula III is α-bromo-γ-butyrolactone.

Suitable acylating agents of formula V are chlorides and bromides of chloroacetic acid, alkoxyacetic acid and tetrahydrofuran-2-carboxylic acid as well as the anhydrides of these acids. Alkoxyacetic acids shall be understood as meaning in particular those containing a $C_1$–$C_4$alkoxy radical such as methoxy, ethoxy, propoxy, isopropoxy, butoxy, sec-butoxy, tert-butoxy and isobutoxy. Preferred acylating agents are methoxyacetyl chloride, chloroacetyl chloride and tetrahydrofuran-2-carboxylic acid chloride, with methoxyacetyl chloride being particularly preferred.

The reaction of a 2,6-dialkylaniline of formula II with a halide of formula III is advantageously carried out in an inert solvent in the presence of an acid acceptor. Suitable inert solvents are aromatic hydrocarbons and hydrogenated hydrocarbons such as benzene, toluene, xylene, chlorobenzene and o-dichlorobenzene, as well as N,N-disubstituted carboxamides such as N,N-dimethylformamide and N'N-dimethyacetamide, and also excess 2,6-dialkylaniline of formula II. Preferred solvents are toluene and xylene. Suitable acid acceptors are inorganic and organic bases such as alkali metal hydroxides, carbonates and bicarbonates, alkaline earth metal hydroxides, carbonates and bicarbonates, triethylamine, pyridine or excess 2,6-dialkylaniline of formula II. A preferred base is sodium carbonate. The reaction temperatures are as a rule in the range from 80° C. to the reflux temperature of the reaction medium. It is advantageous to carry out the alkylation at the reflux temperature of the reaction medium. The reaction of a 2,6-dialkylaniline of formula II with a halide of formula III is therefore preferably carried out in toluene or xylene as solvent, in the presence of sodium carbonate as acid acceptor and at the reflux temperature of the reaction medium.

The reaction of an N-alkyl-2,6-dialkylaniline of formula IV with an acylating agent of formula V is advantageously carried out in an inert solvent in the absence or presence of an acid acceptor. Suitable inert solvents are in particular water-immiscible solvents such as aliphatic and aromatic hydrocarbons and halogenated hydrocarbons. Examples of suitable solvents are hexane, benzene, toluene, xylene, chlorobenzene, methylene chloride, chloroform, carbon tetrachloride and ethylene chloride. Preferred solvents are toluene and xylene.

Suitable acid acceptors in the presence of which the reaction of an N-alkyl-2,6-dialkylaniline of formula IV with an acylating agent of formula V can be carried out are inorganic and organic bases such as alkali metal hydroxides, carbonates and bicarbonates, alkaline earth metal hydroxides, carbonates and bicarbonates, triethylamine and pyridine. The reaction of an N-alkyl-2,6-dialkylaniline of formula IV with an acylating agent of formula V is preferably carried out in the absence of a base, in toluene or xylene and under reduced pressure. Suitable pressures under which the reaction of an N-alkyl-2,6-dialkylaniline of formula IV with an acylating agent of formula V can be carried out are in the range from 50 to 150 mbar, preferably from 60 to 100 mbar.

The chlorination of an N-acyl-N-alkyl-2,6-dialkylaniline of formula VI is also advantageously carried out in an inert solvent. Suitable solvents are in particular lower aliphatic carboxylic acids such as formic acid and acetic acid. Further suitable solvents are chlorinated aromatic and aliphatic hydrocarbons such as chlorobenzene, methylene chloride, chloroform, carbon tetrachloride and ethylene chloride. The carboxylic acids employed as solvents may contain up to 60% by weight of water. A preferred solvent in which the chlorination of an N-acyl-N-alkyl-2,6-dialkylaniline of formula VI can be carried out is formic acid with a water content of up to 40% by weight.

The chlorination is advantageously carried out in the temperature range from 20° to 40° C. The chlorination can also be carried out either at more elevated or at lower temperatures. However, it must be borne in mind that at temperatures above 40° C. increasingly dichlorinated products are formed, whereas at temperatures below 20° C. there is a danger that the reaction will no longer begin immediately on commencement of the introduction of chlorine, but will only start when a relatively high concentration of chlorine has built up. This delayed-start reaction is often very vigorous and it is difficult to control the temperature of the reaction mixture. In this case the formation of dichlorinated products must also be expected.

It is also advantageous to carry out the chlorination in the presence of Lewis acids such as aluminium chloride, iron(III) chloride, boron trifluoride and titanium tetrachloride. Iron(III) chloride is a preferred Lewis acid. The Lewis acids are employed in an amount of 1 to 5% by weight, preferably 1.5 to 2.5% by weight, based on the N-acyl-N-alkyl-2,6-dialkylaniline of formula VI to be chlorinated. The Lewis acids do not as such have a substantial influence on the chlorination, however they greatly increase the solubility in aqeuous formic acid or aqueous acetic acid of the N-acyl-N-alkyl-2,6-dialkylanilines of formula VI to be chlorinated. Therefore, in order to obtain a higher volume yield, it is advisable to add Lewis acids in particular when employoying formic acid or acetic acid as solvent. The chlorination of an N-acyl-N-alkyl-2,6dialkylaniline of formula VI is thus preferably carried out in the temperature range from 20° to 40° C., in formic acid with a water content of up to 40% by weight and in the presence of 1.5 to 2.5% by weight of iron(III) chloride, based on the N-acyl-N-alkyl-2,6-dialkylaniline of formula VI employed.

The chlorination is usually carried out under normal pressure. When using formic acid or acetic acid as solvent, the reaction may be carried out under slightly excess pressure since no gas escapes from the reaction mixture when these solvents are in use.

The process of the present invention makes it possible to prepare the N-acyl-N-alkyl-2,6-dialkyl-3-chloroanilines of formula I from 2,6-dialkylanilines of formula II in simple manner and in a substantially better yield than by the known processes. Compared with the process described in published British patent application No. 2 089 210, which process is based on the chlorination of N-alkyl-2,6-dialkylaniline in the presence of at least 2 moles of a Lewis acid, the use of large amounts of Lewis acid and the concomitant difficulties in working up can be avoided. Compared with the process mentioned at the outset which is based on the chlorination of N-acetyl-2,6-dialkylanilines, two reaction steps can be dispensed with, i.e. the introduction of the acetyl group before chlorination and the removal thereof after chlorination. The N-alkylation of 2,6-dialkylanilines affords better yields than the corresponding N-alkylation of 2,6-dialkyl-3-chloroanilines. Moreover, surprisingly, the chlorinarion of N-acyl-N-alkyl-2,6-dialkylanilines of formula VI affords better yields than the known chlorination of 2,6-dialkylacetanilides. The concept of the present invention makes it possible for the first time time to utilize these advantages. It is an essential feature of this concept that the introduction of the chlorine atom into the 3-position of the phenyl radical is carried out in the final step.

The process of the present invention is illustrated in more detail by the following Example.

EXAMPLE 1

Preparation of N-methoxyacetyl-N-(2-oxotetrahydro-3-furyl)-3-chloro-2,6-dimethylaniline (a) 64 g (0.6 mole) of anhydrous sodium carbonate solution are suspended in a solution of 121 g (1.0 mole) of 2,6-dimethylaniline in 500 ml of xylene. Over 2 hours, 206 g (1.25 moles) of α-bromo-γ-butyrolactone (3-bromo-2-oxotetrahydrofuran) are added to this suspension at reflux temperature (about 140° C.). When the addition of the α-bromo-γ-butyrolactone is complete, the reaction mixture is stirred for 4 hours at room temperature. The water of reaction is removed during the addition of the α-bromo-γ-butyrolactone and during the subsequent stirring. The reaction mixture is then cooled to 50° C., washed first with 200 ml of water and then with 200 ml of 5% hydrochloric acid and subsequently dried by distilling off 50–60 ml of solvent. According to gas chromatographic analysis, the reaction mixture contains 174 g (85% of theory) of N-(2-oxotetrahydro-3-furyl)-2,6-dimethylaniline, part of which precipitates when the reaction mixture cools. The resultant suspension can be further processed direct in the next step. However, the product may also be recovered by distilling off the solvent and crystallising the residue from isopropanol. The melting point is 82°–84° C.

(b) Over 2 hours, 113 g (1.04 moles) of methoxyacetyl chloride are added at 60°–70° C. and under a pressure of 70°–80 mbar to a suspension of 205 g (1.0 mole) of N-(2-oxotetrahydro-3-furyl)-2,6-dimethylaniline in 500 ml of xylene. Towards the end of the addition of methoxyacetyl chloride the reaction mixture begins to boil, with hydrogen chloride gas evolving. When the addition of methoxyacetyl chloride is complete, the reaction mixture is stirred for 3 hours under weak reflux at 60°–65° C. and under a pressure of 70–80 mbar, and the hydrogen chloride evolving during the reaction is removed. Subsequently, half of the xylene is distilled off, the reaction mixture is cooled to 20° C., the precipitated product is filtered off, washed with xylene and dried, affording 263 g (95% of theory) of N-methoxyacetyl-N-(2-oxotetrahydro-3-furyl)-2,6-dimethylaniline with a melting point of 118°–120° C.

(c) Over 2 hours, 74.6 g (1.05 moles) of chlorine are introduced at 25°–30° C. into a solution of 277 g (1.0 mole) of N-methoxyacetyl-N-(2-oxotetrahydro-3-furyl)-2,6-dimethylaniline and 5 g of iron(III) chloride in 300 ml of 85% formic acid. The reaction is exothermic and virtually no gas evolves. When the addition of chlorine is complete, the reaction mixture is stirred for 30 minutes at 25° C., the formic acid is then distilled off in vacuo, the residue is taken up in 500 ml of toluene and the toluenic solution is washed with 100 ml of water. The oily residue obtained after the toluene has been distilled off is crystallised from a mixture of isopropanol and hexane, affording 287 g (92% of theory) of N- methoxyacetyl-N-(2-oxotetrahydro-3-furyl)-3-chloro-2,6-dimethylaniline with a melting point of 80°-82° C.

What is claimed is:

1. A process for the preparation of an N-acyl-N-alkyl-2,6-dialkyl-3-chloroaniline of formula I

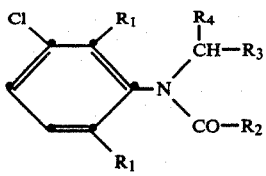

wherein $R_1$ is methyl or ethyl, $R_2$ is alkoxymethyl, chloromethyl or 2-tetrahydrofuryl, $R_3$ is alkoxymethyl, carboxy or alkoxycarbonyl and $R_4$ is hydrogen or methyl and, if $R_3$ is carboxy or alkoxycarbonyl, $R_4$ is also 2-alkoxyethyl and 2-alkoxypropyl, and $R_3$ and $R_4$, together with the carbon atom to which both radicals are attached, may also form a 2-oxotetrahydro-3-furyl radical or a 2-oxo-5-methyltetrahydro-3-furyl radical, which process comprises reacting a 2,6-dialkylaniline of formula II

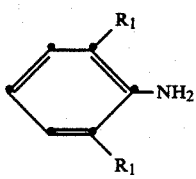

wherein $R_1$ is as defined for formula I, with a halide of formula III

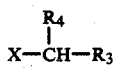

wherein $R_3$ and $R_4$ are as defined for formula I and X is chlorine or bromine, to give an N-alkyl-2,6-dialkylaniline of formula IV

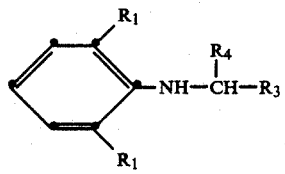

wherein $R_1$, $R_3$ and $R_4$ are as defined for formula I, then reacting the N-alkyl-2,6-dialkylaniline of formula IV with an acylating agent formula V

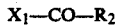

wherein $R_2$ is as defined for formula I and $X_1$ is chlorine, bromine or —O—CO—$R_2$, and subsequently converting the resultant N-acyl-N-alkyl-2,6-dialkylaniline of formula VI

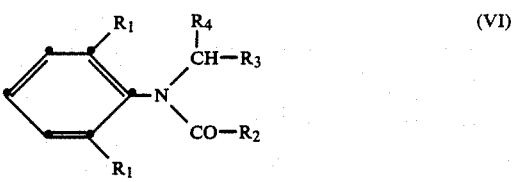

wherein $R_1$, $R_2$, $R_3$ and $R_4$ are as defined for formula I, by reaction with chlorine into an N-acyl-N-alkyl-2,6-dialkyl-3-chloroaniline of formula I.

2. A process according to claim 1, wherein the 2,6-dialkylaniline of formula II is 2,6-dimethylaniline or 2,6-diethylaniline.

3. A process according to claim 2, wherein the 2,6-dialkylaniline of formula II is 2,6-dimethylaniline.

4. A process according to claim 1, wherein the halide of formula III is 2-methoxyethyl chloride, 2-ethoxyethyl chloride, 2-methoxy-1-methylethyl chloride, methyl 2-chloroacetate, ethyl 2-chloroacetate, methyl 2-bromopropionate, ethyl 2-bromopropionate or α-bromo-γ-butyrolactone.

5. A process according to claim 4, wherein the halide of formula III is α-bromo-γ-butyrolactone.

6. A process according to claim 1, wherein the acylating agent of formula V is methoxyacetyl chloride, chloroacetyl chloride or tetrahydrofuran-2-carboxylic acid chloride.

7. A process according to claim 6, whewrein the acylating agent of formula V is methoxyacetyl chloride.

8. A process according to claim 1, wherein the reaction of a 2,6-dialkylaniline of formula II with a halide of formula III is carried out in an inert solvent and in the presence of an acid acceptor.

9. A process according to claim 8, wherein the inert solvent is benzene, toluene, xylene, chlorobenzene, o-dichlorobenzene, N,N-dimethylformamide or N,N-dimethylacetamide.

10. A process according to claim 8, wherein the inert solvent is toluene or xylene.

11. A process according to claim 8, wherein the acid acceptor is an alkali metal hydroxide, carbonate or bicarbonate, an alkaline earth metal hydroxide, carbonate or bicarbonate, triethylamine or pyridine.

12. A process according to claim 8, wherein the acid acceptor is sodium carbonate.

13. A process according to claim 1, wherein the reaction of a 2,6-dialkylaniline of formula II with a halide of formula III is carried out at a temperature in the range from 80° C. to the reflux temperature of the reaction medium.

14. A process according to claim 13, wherein the reaction of a 2,6-dialkylaniline of formula II with a halide of formula III is carried out at the reflux temperature of the reaction medium.

15. A process according to claim 1, wherein the reaction of a 2,6-dialkylaniline of formula II with a halide of formula III is carried out in toluene or xylene as solvent, in the presence of sodium carbonate as acid acceptor and at the reflux temperature of the reaction medium.

16. A process according to claim 1, wherein the reaction of an N-alkyl-2,6-dialkylaniline of formula IV with an acylating agent of formula V is carried out in an inert solvent.

17. A process according to claim 16, wherein the reaction of an N-alkyl-2,6-dialkylaniline of formula IV with an acylating agent of formula V is carried out in hexane, benzene, toluene, xylene, chlorobenzene, methylene chloride, chloroform, carbon tetrachloride or ethylene chloride as solvent.

18. A process according to claim 16, wherein the reaction of an N-alkyl-2,6-dialkylaniline of formula IV with an acylating agent of formula V is carried out in toluene or xylene as solvent.

19. A process according to claim 1, wherein the reaction of an N-alkyl-2,6-dialkylaniline of formula IV with an acylating agent of formula V is carried out in the absence of a base, in toluene or xylene as solvent and under reduced pressure.

20. A process according to claim 1, wherein the chlorination of an N-acyl-N-alkyl-2,6-dialkylaniline of formula VI is carried out in an inert solvent.

21. A process according to claim 20, wherein the inert solvent is formic acid, acetic acid, chlorobenzene, methylene chloride, chloroform, carbon tetrachloride or ethylene chloride.

22. A process according to claim 20, wherein the inert solvent is formic acid or acetic acid with a water content of up to 40% by weight.

23. A process according to claim 1, wherein the chlorination of an N-acyl-N-alkyl-2,6-dialkylaniline of formula VI is carried out in the temperature range from 20° to 40° C.

24. A process according to claim 1, wherein the chlorination of an N-acyl-N-alkyl-2,6-dialkylaniline of formula VI is carried out in the presence of 1 to 5% by weight of a Lewis acid.

25. A process according to claim 24, wherein the Lewis acid is aluminium chloride, iron(III) chloride, boron trifluoride or titanium tetrachloride.

26. A process according to claim 24, wherein the Lewis acid is iron(III) chloride.

27. A process according to claim 1, wherein the chlorination of an N-acyl-N-alkyl-2,6-dialkylaniline of formula VI is carried out in the temperature range from 20° to 40° C., in formic acid with a water content of up to 40% by weight and in the presence of 1.5 to 2.5% by weight of iron(III) chloride, based on the N-acyl-N-alkyl-2,6-dialkylaniline of formula VI employed.

* * * * *